US008569471B2

(12) United States Patent
Phillips et al.

(10) Patent No.: US 8,569,471 B2
(45) Date of Patent: Oct. 29, 2013

(54) STEM CELL BEACON

(75) Inventors: M. Ian Phillips, Claremont, CA (US);
Yao Liang Tang, Claremont, CA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/299,991

(22) Filed: Nov. 18, 2011

(65) Prior Publication Data

US 2012/0164212 A1    Jun. 28, 2012

Related U.S. Application Data

(63) Continuation of application No. 10/567,275, filed as application No. PCT/US2004/026196 on Aug. 11, 2004, now abandoned.

(60) Provisional application No. 60/513,067, filed on Oct. 21, 2003, provisional application No. 60/494,184, filed on Aug. 11, 2003, provisional application No. 60/513,657, filed on Oct. 23, 2003, provisional application No. 60/494,185, filed on Aug. 11, 2003.

(51) Int. Cl.
| C07H 21/00 | (2006.01) |
| C07H 21/04 | (2006.01) |
| C07H 21/02 | (2006.01) |
| C12P 21/06 | (2006.01) |
| C12N 7/00 | (2006.01) |
| C12N 7/01 | (2006.01) |
| C12N 15/00 | (2006.01) |

(52) U.S. Cl.
USPC ....... 536/23.4; 536/23.1; 536/23.5; 435/69.1; 435/235.1; 435/320.1; 435/455

(58) Field of Classification Search
None
See application file for complete search history.

(56) References Cited

U.S. PATENT DOCUMENTS

| 2002/0094327 A1 | 7/2002 | Petersen |
| 2003/0027751 A1 | 2/2003 | Kovesdi et al. |
| 2007/0117766 A1 | 5/2007 | Phillips et al. |

FOREIGN PATENT DOCUMENTS

| WO | WO 00/50048 A3 | 8/2000 |
| WO | WO 2004/024867 A2 | 3/2004 |
| WO | WO 2005/017164 A1 | 2/2005 |

OTHER PUBLICATIONS

Abruzzese, R. et al. "Ligand-dependent regulation of vascular endothelial growth factor and erythropoietin expression by a plasmid-based autoinducible GeneSwitch system" *Mol. Therapy*, 2000, 2:276-287.

Chen, H. et al. "Protection against ischemia/reperfusion injury and myocardial dysfunction by antisense-oligodeoxynucleotide directed at angiotensin-converting enzyme mRNA" *Gene Ther.*, 2001, 8:804-810.

Chen, H. et al. "Protection against myocardial dysfunction induced by global ischemia-reperfusion by antisense-oligodeoxynucleotides directed at $\beta_1$-adrenoceptor mRNA" *J. Pharmacol. Exp. Ther.*, 2000, 294:722-727.

Conget, P. and Minguell, J. "Adenoviral-mediated gene transfer into ex vivo expanded human bone marrow mesenchymal progenitor cells" *Exp. Hematol.*, 2000, 28:382-390.

Davani, S. et al. "Mesenchymal progenitor cells differentiate into an endothelial phenotype, enhance vascular density, and improve heart function in a rat cellular cardiomyoplasty model" *Circulation*, 2003, 108(Suppl. II):II253-II258.

Franz, W.M. et al. "Heart-specific targeting of firefly luciferase by the myosin light chain-2 promoter and developmental regulation in transgenic mice" *Circ. Res.*, 1993, 73:629-638.

Giniger, E. et al. "Specific DNA binding of GAL4, a positive regulatory protein of yeast" *Cell*, 1985, 40:767-774.

Gu, J. et al. "Tumor-specific transgene expression from the human telomerase reverse transcriptase promoter enables targeting of the therapeutic effects of the *Bax* gene to cancers" *Cancer Res.*, 2000, 60:5359-5364.

Haberman, R. et al. "Inducible long-term gene expression in brain with adeno-associated virus gene transfer" *Gene Therapy*, 1998, 5:1604-1611.

Halaby, I. et al. "Glucocorticoid-regulated VEGF expression in ischemic skeletal muscle" *Mol. Therapy*, 2002, 5:300-306.

Huang, L.E. et al. "Regulation of hypoxia-inducible factor $1\alpha$ is mediated by an $O_2$-dependent degradation domain via the ubiquitin-proteasome pathway" *Proc Natl Aced Sci USA*, 1998, 95:7987.

Kagiyama, T. et al. "Expression of angiotensin type 1 and 2 receptors in brain after transient middle cerebral artery occlusion in rats" *Regul. Pept.*, 2003, 110:241-247.

Keegan, L. et al. "Separation of DNA binding from the transcription-activating function of a eukaryotic regulatory protein" *Science*, 1986, 231:699-704.

Kimura, B. et al. "Attenuation of hypertension and heart hypertrophy by adeno-associated virus delivering angiotensinogen antisense" *Hypertension*, 2001, 37:376-380.

Kircheis, R. et al. "Polyethylenimine/DNA complexes shielded by transferring target gene expression to tumors after systemic application" *Gene Ther.*, 2001, 8:28-40.

(Continued)

*Primary Examiner* — Valarie Bertoglio
(74) *Attorney, Agent, or Firm* — Saliwanchik, Lloyd & Eisenschenk

(57) ABSTRACT

The invention relates to methods and compositions for selectively directing stem cells to a target tissue within a subject using a system that employs one or more vectors that contain a gene switch/biosensor, a tissue-specific promoter, a gene encoding a stem cell-attracting chemokine, and a gene amplification system. In one embodiment, a stem cell-attracting chemokine is expressed in damaged tissue using a stimulus-responsive vector system. The stimulus can be a physiological stimulus associated with cell injury, such as hypoxia or elevated glucose levels, for example. Expression of the chemokine increases the trafficking of stem cells to the damaged tissue.

15 Claims, 18 Drawing Sheets
(7 of 18 Drawing Sheet(s) Filed in Color)

(56) References Cited

OTHER PUBLICATIONS

Koh, G.Y. et al. "Targeted expression of transforming growth factor-β1 in intracardiac grafts promotes vascular endothelial cell DNA synthesis" *J. Clin. Invest.*, 1995, 95:114-121.
Kollet, O. et al. "HGF, SDF-1, and MMP-9 are involved in stress-induced human $CD34^+$ stem cell recruitment to the liver" *J. Clin. Invest.*, 2003, 112:160-169.
Mangi, A.A. et al. "Mesenchymal stem cells modified with Akt prevent remodeling and restore performance of infracted hearts" *Nat. Med.*, 2003, 9:1195-1201.
Melo, L. et al. "Gene therapy strategy for long-term myocardial protection using adeno-associated virus-mediated delivery of heme oxygenase gene" *Circulation*, 2002, 105:602-607.
Ogris, M. et al. "The size of DNA/transferring-PEI complexes is an important factor for gene expression in cultured cells" *Gene Ther.*, 1998, 5:1425-1433.
Phillips, M.I. "Gene therapy for hypertension: Antisense inhibition with adeno-associated viral fector delivery targeting angiotensin II type 1 receptor messenger ribonucleic acid" *Am. J. Cardiol.*, 1998, 82(10A):60S-62S.
Phillips, M.I. "Somatic gene therapy for hypertension" *Braz. J. Med. Biol. Res.*, 2000, 33:715-721.
Phillips, M.I. "Gene therapy for hypertension: sense and antisense" *Expert Opin. Biol. Ther.*, 2001, 1(4):655-662, abstract.
Phillips, M.I. "Is gene therapy for hypertension possible?" *Hypertension*, 1999, 33:8-13.
Phillips, M.I. "Gene therapy for hypertension: The preclinical data" *Hypertension*, 2001, 38(3 Pt 2):543-548.
Phillips, M.I. et al. "Vigilant vector: Heart-specific promoter in an adeno-associated virus vector for cardioprotection" *Hypertension*, 2002, 39(2 Pt 2):651-655.
Phillips, M.I. "Gene therapy for hypertension: The preclinical data" *Methods Enzymol.*, 2002, 346:3-13.
Ponnazhagan, S. et al. "Adeno-associated virus type 2-mediated transduction of murine hematopoietic cells with long-term repopulating ability and sustained expression of a human globin gene in vivo" *J. Virology*, 1997, 71:3098-3104.
Qiao, J. et al. "Tumor-specific transcriptional targeting of suicide gene therapy" *Gene Therapy*, 2002, 9:168-175.
Ruan, H. et al. "A hypoxia-regulated adeno-associated virus vector for cancer-specific gene therapy" *Neoplasia*, 2001, 3:255-263.
Schmitz, M.L. and Baeuerle, P.A. "The p65 subunit is responsible for the strong transcription activating potential of NF-κB" *EMBO J.*, 1991, 10:3805-3817.
Semenza, G. et al. "Hypoxia response elements in the aldolase A, Enolase 1, and lactate dehydrogenase A gene promoters contain essential binding sites for hypoxia-inducible factor 1" *J Biol Chem.*, 1996, 271:32529-32537.
Shake, J.G. et al. "Mesenchymal stem cell implantation in a swine myocardial infarct model: Engraftment and function effects" *Ann. Thorac. Surg.*, 2002, 73:1919-1925.
Sirtori, C.R. "New targets for lipid lowering and atherosclerosis prevention" *Pharmacol. Ther.*, 1995, 67:433-447.
Smith-Arica, J.R. et al. "Switching on and off transgene expression within lactotrophic cells in the anterior pituitary gland in vivo" *Endocrinology*, 2001, 142:2521-2532.
Strauer, B.E. and Kornowski, R. "Stem cell therapy in perspective" *Circulation*, 2003, 107:929-934.
Tang, X. et al. "Intravenous angiotensinogen antisense in AAV-based vector decreases hypertension" *Am. J. Physiol.*, 1999, 277(6 Pt 2):H2392-H2399.
Tang, Y. et al. "Paracrine action enhances the effects of autologous mesenchymal stem cell transplantation on vascular regeneration in rat model of myocardial infarction" *Ann Thorac. Surg.*, 2005, 80:229-236.
Tang, Y. et al. "A hypoxia-inducible vigilant vector system for activating therapeutic genes in ischemia" *Gene Ther.*, 2005, 12:1163-1170.
Tang, Y. et al. "Hypoxia inducible double plasmid system for myocardial ischemia gene therapy" *Hypertension*, 2002, 39(2 Pt 2):695-698.
Tang, Y. et al. "Protection from ischemic heart injury by a vigilant heme oxygenase-1 plasmid system" *Hypertension*, 2004, 43:746-751.
Tang, Y. et al. "Improved graft mesenchymal stem cell survival in ischemic heart with a hypoxia-regulated heme oxygenase-1 vector" *J. Am. Colt Cardiol.*, 2005, 46:1339-1350.
Tang, Y. et al. "A vigilant, hypoxia-regulated heme oxygenase-1 gene vector in the heart limits cardiac injury after ischemia-reperfusion in vivo" *J. Cardiovasc. Pharmacol. Ther.*, 2005, 10:251-263.
Tang, Y. et al. "Vigilant vectors: adeno-associated virus with a biosensor to switch on amplified therapeutic genes in specific tissues in life-threatening diseases" *Methods*, 2002, 28:259-266.
Tang, Y. et al. "Autologous mesenchymal stem cell transplantation induce VEGF and neovascularization in ischemic myocardium" *Regul. Pept.*, 2004, 117:3-10.
Tang, Y. et al. "Mobilizing of haematopoietic stem cells to ischemic myocardium by plasmid mediated stromal-cell-derived factor-1α (SDF-1α) treatment" *Regul. Pept.*, 2005, 125:1-8.
Woo, Y.J. et al. "Recombinant adenovirus-mediated cardiac gene transfer of superoxide dismutase and catalase attenuates postischemic contractile dysfunction" *Circulation*, 1998, 98:II255-II261.
Wu, P. et al. "Adeno-associated virus vector-mediated transgene integration into neurons and other nondividing cell targets" *J. Virol.*, 1998, 72:5919-5926.
Yamaguchi, J. et al. "Stromal cell-derived factor-1 effects on ex vivo expanded endothelial progenitor cell recruitment for ischemic neovascularization" *Circulation*, 2003, 107:1322-1328.
Yang, B.C. et al. "Critical role of AT1 receptor expression after ischemia/reperfusion in isolated rat hearts: Beneficial effect of antisense oligodeoxynucleotides directed at AT1 receptor mRNA", 1998, *Circ. Res.* 83:552-559.
Yang, B.C. et al. "Increase in angiotensin II type 1 receptor expression immediately after ischemia-reperfusion in isolated rat hearts" *Circulation*, 1997, 96:922-926.
Zvaritch, E. et al. "The transgenic expression of highly inhibitory monomeric forms of phospholamban in mouse heart impairs cardiac contractility" *J. Biol. Chem.*, 2000, 275:14985-14991.
Christoforou, N. and Gearhart, J.D. "Stem cells and their potential in cell-based cardiac therapies" *Prog. Cardiov. Dis.*, 2007, 49(6):396-413.
Inverardi, L. and Ricordi, C. "Cell Transplantation" in Transplantation Biology: Cellular and Molecular Aspects, Tillney et al., Eds., Lippincott-Raven Publishers, 1996, Ch. 56, pp. 679-687.
Verma, I.M. and Somia, N. "Gene therapy—promises, problems and prospects" *Nature*, 1997, 389:239-242.
Nathwani, A.G. et al. "Efficient gene transfer into human cord blood $CD34^+$ cells and the $CD34^+CD38^-$ subset using highly purified recombinant adeno-associated viral vector preparations that are free of helper virus and wild-type AAV" *Gene Therapy*, 2000, 7:183-195.

US 8,569,471 B2

STEM CELL BEACON

CROSS-REFERENCE TO RELATED APPLICATIONS

The present application is a continuation of U.S. application Ser. No. 10/567,275, filed May 9, 2007, which is the National Stage of International Application Number PCT/US2004/026196, filed Aug. 11, 2004, which claims the benefit of U.S. Provisional Application Ser. No. 60/513,067, filed Oct. 21, 2003, U.S. Provisional Application Ser. No. 60/494,184, filed Aug. 11, 2003, U.S. Provisional Application Ser. No. 60/513,657, filed Oct. 23, 2003, and U.S. Provisional Application Ser. No. 60/494,185, filed Aug. 11, 2003, each of which are hereby incorporated by reference herein in their entirety, including any figures, tables, nucleic acid sequences, amino acid sequences, and drawings.

GOVERNMENT SUPPORT

This invention was made with government support under grant number 5R37HL2733423 awarded by the National Institutes of Health. The government has certain rights in the invention.

BACKGROUND OF THE INVENTION

Several common diseases such as heart failure and type 1 diabetes are characterized by cellular degeneration in the affected organ. While a variety of drugs have been developed that treat the symptoms of such diseases, in many cases these drugs do not correct the underlying cellular degeneration causing the diseases, but rather merely ameliorate some of the symptoms of the disease. A theoretically more preferable method to treat the disease is to replace the degenerating or dead cells with healthy cells, e.g., by organ transplantation. Although successful in many cases, organ transplantation remains a complex process replete with both clinical and practical problems such as risk of immune system-mediated rejection and lack of donor organs.

BRIEF SUMMARY OF THE INVENTION

The invention relates to the fields of molecular biology, gene therapy, and medicine. More particularly, the invention relates to compositions and methods for delivering and amplifying expression of a gene encoding a stem cell-attracting chemokine in a specific tissue.

The invention relates to methods and compositions for selectively directing stem cells to a target tissue within a subject using a system that employs one or more vectors that contain a gene switch/biosensor, a tissue-specific promoter, a gene encoding a stem cell-attracting chemokine (e.g., stromal-derived factor (SDF)-1α, stem cell factor (SCF)) and a gene amplification system. The gene switch/biosensor allows expression of the chemokine-encoding gene to be regulated by a stimulus (e.g., a physiological stimulus such as one associated with cellular degeneration). Thus, expression of a stem cell-attracting chemokine can be increased in response to a particular event (e.g., increase in glucose concentration, decrease in oxygen concentration and mechanical stretch in vessel wall of hypertension, etc.). The high local concentrations of the stem cell-attracting chemokine will then cause stem cells to be recruited into and/or retained by the target tissue at a greater than normal rate. Once in the target tissue, the stem cells can differentiate (with or without the help of other agents such as morphogenesis) into new cells to replace the damaged cells and restore organ function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5B is a photomicrograph of a cross section of vigilant hSDF-1α plasmid-treated ischemic myocardium. Ischemic cardiomyocytes in the peri-infarction zone expressed hSDF-1α (large arrowheads). The transplanted Lin$^-$c-kit$^+$ stem cells (small arrowheads) are clustered proximal to the hSDF-1α positive zone. Cytoplasm was recognized by the red fluorescence of PKH26. FIG. 5D is a confocal image (100×) of the same specimen as in FIG. 5C. Ischemic cardiomyocytes express hSDF-1α (large arrowhead). The transplanted Lin$^-$c-kit$^+$ stem cells (small arrowheads) surround the hSDF-1α positive cardiomyocytes. FIG. 5A is ischemic myocardium without vigilant hSDF-1α plasmid treatment. Less hSDF-1α was expressed in ischemic tissue and few PKH26-labeled stem cells were attracted to ischemic myocardium (FIG. 5B).

DETAILED DESCRIPTION OF THE INVENTION

Figure 1:
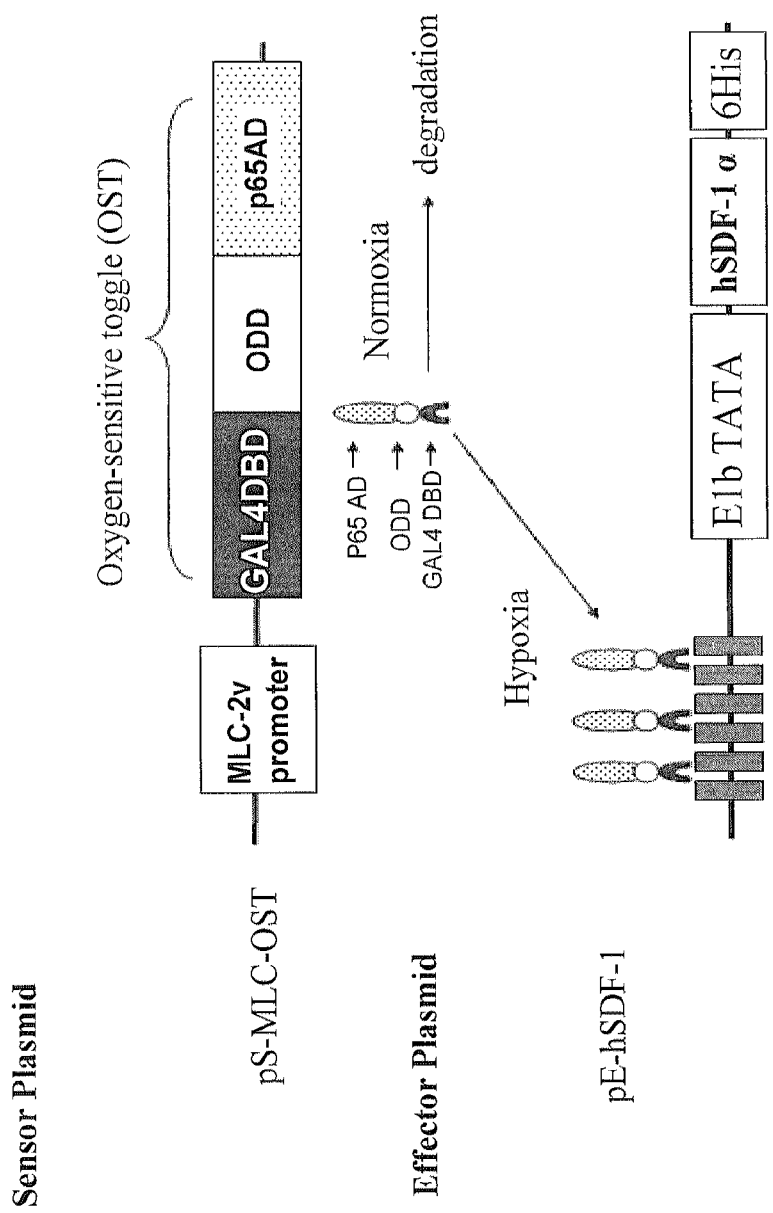
FIG. 1 is a schematic illustration of a double plasmid model for stem cell beacon vector with a hypoxia switch. In the double plasmid model, the cardiac promoter controls an oxygen-sensitive transactivator. The transactivator produces a fusion protein which binds to the inducible promoter and activates transcription of stem cell acting chemokine, SDF-1α in the second plasmid. The oxygen-sensitive chimeric transactivator (GAL4/ODD/p65) is expressed by the transactivator plasmid under the control of the MLC-2v promoter. It can accumulate under hypoxia and activate the inducible promoter containing the GAL4 upstream activation sequence (UAS) in the reporter plasmid.

The invention provides a system for regenerating tissue by directing stem cells to a damaged organ. The system involves delivering to a target tissue, vectors that express a stem cell-attracting chemokine in response to a stimulus that is present in injured but not healthy tissue. The occurrence of a cell-injuring event thus results in production of the stem cell-attracting chemokine at the site of injury, and consequently increased trafficking of stem cells to the injured tissue. Differentiation of the stem cells at this site results in replacement of damaged cells with healthy cells—a process that results in organ regeneration.

The below described preferred embodiments illustrate adaptations of these compositions and methods. Nonetheless, from the description of these embodiments, other aspects of the invention can be made and/or practiced based on the description provided below.

Biological Methods.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy Methods: ed. M. I. Phillips, Vol. 436, Methods in Enzymology, Academic Press, 2002; Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Vectors.

The invention employs one or more vectors to express a stem cell-attracting chemokine in response to a stimulus that is present in injured, but not healthy, tissue. A variety of different vectors might be used depending on the particular application. A preferred system of the invention uses one or more vectors that contain a gene switch/biosensor, a tissue-specific promoter operably linked to a gene encoding a stem cell-attracting chemokine, and a gene amplification system. The gene switch/biosensor allows transgene expression to be regulated by a stimulus (e.g., a physiological stimulus such as hypoxia or high glucose levels). Thus, for example, expression of the gene encoding a stem cell-attracting chemokine can be modulated in response to a particular event (e.g., infarction or onset of diabetes). The tissue-specific promoter allows preferential expression of the gene encoding the stem cell-attracting chemokine in a given target tissue, thereby avoiding expression in other tissues that might be harmful to the subject. The gene amplification system allows a sufficient amount of the gene encoding a stem cell-attracting chemokine to be produced to cause a desired result (e.g., recruitment of stem cells to damaged tissue).

The gene switch/biosensor portion of the system can be any suitable construct that is activated in response to a stimulus associated with cell injury. In the examples described below and in FIG. 1, the gene switch/biosensor is a transactivator plasmid that includes a cardiac-specific promoter linked to a sequence encoding an oxygen-sensitive chimeric transactivator that includes a GAL4 DNA-binding domain (DBD), an oxygen-dependent degradation domain (ODD), and a p65 activation domain (p65 AD). In response to hypoxia, the transactivator binds to the GAL4 UAS sequence in the reporter plasmid (which contains a gene encoding hSDF-1α operably linked to a GAL4 UAS).

In addition to oxygen-sensitive constructs, a number of other gene switch/biosensors are contemplated for use in the invention. Such gene switch/biosensors include a glucose switch based on the Krebs cycle (e.g., glucose response element or other glucose regulated elements), a mechanical stretch switch based on an epithelial sodium channel (ENaC), and a hypoxia response element (HRE).

The gene switch/biosensor portion of the system may include tissue-specific regulatory elements to direct tissue-specific expression of a stem cell-attracting chemokine gene. For example, to express genes specifically in the heart, a number of cardiac-specific regulatory elements can be used. An example of a cardiac-specific promoter is the ventricular form of MLC-2v promoter (see, Zhu et al., Mol. Cell Biol. 13:4432-4444, 1993; Navankasattusas et al., Mol. Cell Biol. 12:1469-1479, 1992) or a variant thereof such as a 281 bp fragment of the native MLC-2v promoter (nucleotides –264 to +17, Genebank Accession No. U26708). Examples of other cardiac-specific promoters include alpha myosin heavy chain (Minamino et al., Circ. Res. 88:587-592, 2001) and myosin light chain-2 (Franz et al., Circ. Res. 73:629-638, 1993).

In other applications, promoters that confer gene expression specific to tissues other than the heart may be used. Promoters that are kidney-specific include CLCN5 (Tanaka et al., Genomics 58:281-292, 1999), renin (Sinn et al., Physical Genomics 3:25-31, 2000), androgen-regulated protein, sodium-phosphate cotransporter, renal cytochrome P-450, parathyroid hormone receptor and kidney-specific cadherin.

See *Am. J. Physiol. Renal Physiol.* 279:F383-392, 2000. The E-cadherin promoter directs expression specific to epithelial cells (Behrens et al., *PNAS* 88:11495-11499, 1991) while the Estrogen receptor (ER) 3 gene promoter directs expression specifically to the breast epithelium (Hopp et al., *J. Mammary Gland Biol. Neoplasia* 3:73-83, 1998). Endothelial cell gene promoters include endoglin and ICAM-2. See Velasco et al., *Gene Ther.* 8:897-904, 2001. Liver-specific promoters include the human phenylalanine hydroxylase (PAH) gene promoters (Bristeau et al., *Gene* 274:283-291, 2001), hB1F (Zhang et al., *Gene* 273:239-249, 2001), and the human C-reactive protein (CRP) gene promoter (Ruther et al., *Oncogene* 8:87-93, 1993). An example of a muscle-specific gene promoter is human enolase (ENO3). Peshavaria et al., *Biochem. J.* 292(Pt 3):701-704, 1993. A number of brain-specific promoters may be useful in the invention and include the thy-1 antigen and gamma-enolase promoters (Vibert et al., *Eur. J. Biochem.* 181:33-39, 1989), the glial-specific glial fibrillary acidic protein (GFAP) gene promoter (Cortez et al., *J. Neurosci. Res.* 59:39-46, 2000), and the human FGF1 gene promoter (Chiu et al., *Oncogene* 19:6229-6239, 2000). The GATA family of transcription factors have promoters directing neuronal and thymocyte-specific expression. See Asnagli et al., *J. Immunol.* 168:4268-4271, 2002. An example of a pancreas-specific promoter is the pancreas duodenum homeobox 1 (PDX-1) promoter. Samara et al., *Mol. Cell Biol.* 22:4702-4713, 2002.

The vectors of the invention include a gene encoding a stem-cell attracting chemokine. Any such chemokine-encoding gene may be used in the invention. For example, genes such as SCF, vascular endothelial growth factor (VEGF), granulocyte colony-stimulating factor (G-CSF), and integrins may be used. For the applications described in the Examples section, a preferred gene encoding a stem-cell attracting chemokine is one that encodes SDF-1α, an alpha-chemokine for hematopoietic stem cells and endothelial progenitor cells. The sequences of a number of different native mammalian SDF-1α proteins are known, including human, rat, mouse, and cat. See, e.g., Shirozu et al., Genomics, 28:495, 1995; Tashiro et al., Science 261:600, 1993; Nishimura et al., Eur. J. Immunogenet. 25:303, 1998; and GenBank Accession No. AF189724.

The vector(s) of the invention features a gene amplification system that provides a high level of tissue-specific chemokine gene expression (tissue-specific promoters typically do not allow high levels of gene expression compared to non-tissue specific promoters such as the CMV promoter). In the examples described herein, gene amplification is achieved using a dual plasmid system, wherein, in response to a signal, a transactivator plasmid is induced to express a transactivator complex that binds a regulatory element on a reporter plasmid to cause a high level of expression of the chemokine gene.

The vector(s) of the invention may also include other regulatory sequences including insulators, silencers, enhancers, initiation sites, internal ribosome entry site elements, termination signals and polyA tails. An example of a cardiac-specific enhancer is alpha BE-4. Gopal-Srivastava et al., 15:7081-7090, 1995.

Vector Delivery.

The vector(s) of the invention may be delivered to target tissues in any suitable manner. Several methods are known. For example, as described in the Examples section below, plasmid vectors may simply be injected into a target tissue.

Other methods for physically introducing plasmids might also be used, e.g., the particle bombardment method (see Yang et al., *Mol. Med. Today* 2:476-481 1996 and Davidson et al., *Rev. Wound Repair Regen.* 6:452-459, 2000), electroporation (see, Preat, V., *Ann. Pharm. Fr.* 59:239-244 2001), and cationic lipid-based methods (see, Feigner et al., *Ann. N.Y. Acad. Sci.* 772:126-139, 1995 and Lasic and Templeton, *Adv. Drug Delivery Rev.* 20:221-266, 1996).

In various embodiments of the invention, the nucleic acid constructs of the invention are introduced into viral vectors. Viral vector methods and protocols are reviewed in Kay et al. *Nature Medicine* 7:33-40, 2001. Preferred viral vectors for use in the invention are recombinant adeno-associated virus (AAV) vectors. See, e.g., Tal, J., *J. Biomed. Sci.* 7:279-291, 2000 and Monahan and Samulski, *Gene Therapy* 7:24-30, 2000. In addition to AAV, other viruses may be used to create vectors useful in the invention. A list of such viruses include adenovirus (see, W. C. Russell, *Journal of General Virology* 81:2573-2604, 2000, and Bramson et al., *Curr. Opin. Biotechnol.* 6:590-595, 1995), herpes simplex virus (see, Cotter and Robertson, *Curr. Opin. Mol. Ther.* 1:633-644, 1999), lentiviruses (see, Vigna and Naldini, *J. Gene Med.* 5:308-316, 2000 and Miyoshi et al., *J. Virol.* 72:8150-8157, 1998), retroviruses (see Hu and Pathak, *Pharmacol. Rev.* 52:493-511, 2000 and Fong et al., *Crit. Rev. Ther. Drug Carrier Syst.* 17:1-60, 2000), and others (e.g., alphaviruses such as Semliki Forest Virus and Sindbis Virus).

The presence of exogenous nucleic acid constructs in cells in a target tissue can be monitored by conventional methods. For example, vector-transduced cells can be assessed by PCR, flow cytometry and immunochemistry.

Target Cells (Tissues) for Introduction of Vectors In Vitro (Ex Vivo) or In Vivo.

Cells genetically modified with the vectors of the invention can range in plasticity from totipotent or pluripotent stem cells (e.g., adult or embryonic), precursor or progenitor cells, to highly specialized cells, such as those of the central nervous system (e.g., neurons and glia), pancreas, heart, lung, and liver. Stem cells can be obtained from a variety of sources, including embryonic tissue, fetal tissue, adult tissue, umbilical cord blood, peripheral blood, bone marrow, and brain, for example. Methods and markers commonly used to identify stem cells and to characterize differentiated cell types are described in the scientific literature (e.g., Stem Cells: Scientific Progress and Future Research Directions, Appendix E1-E5, report prepared by the National Institutes of Health, June, 2001). The list of adult tissues reported to contain stem cells is growing and includes bone marrow, peripheral blood, umbilical cord blood, brain, spinal cord, dental pulp, blood vessels, skeletal muscle, epithelia of the skin and digestive system, cornea, retina, liver, and pancreas.

There are over 200 cell types in the human body, and the vectors of the subject invention can be introduced into any of them. A non-exhaustive list of cell types within into which vectors containing a nucleic acid sequence encoding a stem cell-attracting chemokine may be introduced is shown in Table 1. Other examples of cell types that can be genetically modified with the vectors of the invention include those disclosed by Spier R. E. et al., eds., (2000) *The Encyclopedia of Cell Technology*, John Wiley & Sons, Inc., and Alberts B. et al., eds., (1994) *Molecular Biology of the Cell*, 3$^{rd}$ ed., Garland Publishing, Inc., e.g., pages 1188-1189.

TABLE 1

Examples of Target Cells

Keratinizing Epithelial Cells keratinocyte of epidermis
basal cell of epidermis

TABLE 1-continued

Examples of Target Cells keratinocyte of fingernails and toenails
basal cell of nail bed
hair shaft cells
    medullary
    cortical
    cuticular
hair-root sheath cells
    cuticular
    of Huxley's layer
    of Henle's layer
    external
hair matrix cell
Cells of Wet Stratified Barrier Epithelia surface epithelial cell of stratified squamous epithelium of cornea tongue,
oral cavity, esophagus, anal canal, distal urethra, vagina
basal cell of these epithelia
cell of urinary epithelium
Epithelial Cells Specialized for Exocrine Secretion cells of salivary gland
    mucous cell
    serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of apocrine sweat gland
cell of gland of Moll in eyelid
cell of sebaceous gland, secreting lipid-rich sebum
cell of Bowman's gland in nose
cell of Brunner's gland in duodenum, secreting alkaline solution of
mucus and enzymes
cell of seminal vesicle, secreting components of seminal fluid, including
fructose
cell of prostate gland, secreting other components of seminal fluid
cell of bulbourethral gland, secreting mucus
cell of Bartholin's gland, secreting vaginal lubricant
cell of gland of Littré, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung
Cells Specialized for Secretion of Hormones cells of anterior pituitary, secreting
    growth hormone
    follicle-stimulating hormone
    luteinizing hormone
    prolactin
    adrenocorticotropic hormone
    thyroid-stimulating hormone
cell of intermediate pituitary, secreting melanocyte-stimulating hormone
cells of posterior pituitary, secreting
    oxytocin
    vasopressin
cells of gut and respiratory tract, secreting
    serotonin
    endorphin
    somatostatin
    gastrin
    secretin
    cholecystokinin
    insulin
    glucagons
    bombesin
cells of thyroid gland, secreting
    thyroid hormone
    calcitonin TABLE 1-continued Examples of Target Cells cells of parathyroid gland, secreting
    parathyroid hormone
    oxyphil cell
cells of adrenal gland, secreting
    epinephrine
    norepinephrine
    steroid hormones
        mineralocorticoids
        glucocorticoids
cells of gonads, secreting
    testosterone
    estrogen
    progesterone
cells of juxtaglomerular apparatus of kidney
    juxtaglomerular cell
    macula densa cell
    peripolar cell
    mesangial cell
Epithelial Absorptive Cells in Gut, Exocrine Glands, and Urogenita Tract brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage hepatocyte
fat cells (e.g., adipocyte)
    white fat
    brown fat
    lipocyte of liver
Epithelial Cells Serving Primarily a Barrier Function, Lining the Lung,
Gut, Exocrine Glands, and Urogenital Tract type I pneumocyte
pancreatic duct cell
nonstriated duct cell of sweat gland, salivary gland, mammary gland, etc.
parietal cell of kidney glomerulus
podocyte of kidney glomerulus
cell of thin segment of loop of Henle
collecting duct cell
duct cell of seminal vesicle, prostate gland, etc.
Epithelial Cells Lining Closed Internal Body Cavities vascular endothelial cells of blood vessels and lymphatics (e.g.,
microvascular cell)
    fenestrated
    continuous
    splenic
synovial cell
serosal cell
squamous cell lining perilymphatic space of ear
cells lining endolymphatic space of ear
    squamous cell
    columnar cells of endolymphatic sac
        with microvilli
        without microvilli
    "dark" cell
    vestibular membrane cell
    stria vascularis basal cell
    stria vascularis marginal cell
    cell of Claudius
    cell of Boettcher
choroid plexus cell
squamous cell of pia-arachnoid
cells of ciliary epithelium of eye
    pigmented
    nonpigmented
corneal "endothelial" cell
Ciliated Cells with Propulsive Function of respiratory tract
of oviduct and of endometrium of uterus TABLE 1-continued Examples of Target Cells of rete testis and ductulus efferens
of central nervous system
Cells Specialized for Secretion of Extracellular Matrix epithelial:
   ameloblast
   planum semilunatum cell of vestibular apparatus of ear
   interdental cell of organ of Corti
nonepithelial:
   fibroblasts
   pericyte of blood capillary (Rouget cell)
   nucleus pulposus cell of intervertebral disc
   cementoblast/cementocyte
   odontoblast/odontocyte
   chondrocytes
      of hyaline cartilage
      of fibrocartilage
      of elastic cartilage
   osteoblast/osteocyte
   osteoprogenitor cell
   hyalocyte of vitreous body of eye
   stellate cell of perilymphatic space of ear
Contractile Cells skeletal muscle cells
   red
   white
   intermediate
   muscle spindle-nuclear bag
   muscle spindle-nuclear chain
   satellite cell
heart muscle cells
   ordinary
   nodal
   Purkinje fiber
   Cardiac valve tissue
smooth muscle cells
myoepithelial cells:
   of iris
   of exocrine glands
Cells of Blood and Immune System red blood cell (erythrocyte)
megakaryocyte
macrophages
   monocyte
   connective tissue macrophage
   Langerhan's cell
   osteoclast
   dendritic cell
   microglial cell
neutrophil
eosinophil
basophil
mast cell
plasma cell
T lymphocyte
   helper T cell
   suppressor T cell
   killer T cell
B lymphocyte
   IgM
   IgG
   IgA
   IgE
killer cell
stem cells and committed progenitors for the blood and immune system
Sensory Transducers photoreceptors
   rod
   cones
      blue sensitive
      green sensitive
      red sensitive
hearing
   inner hair cell of organ of Corti
   outer hair cell of organ of Corti acceleration and gravity
   type I hair cell of vestibular apparatus of ear
   type II hair cell of vestibular apparatus of ear
taste
   type II taste bud cell
smell
   olfactory neuron
   basal cell of olfactory epithelium
blood pH
   carotid body cell
      type I
      type II
touch
   Merkel cell of epidermis
   primary sensory neurons specialized for touch
temperature
   primary sensory neurons specialized for temperature
      cold sensitive
      heat sensitive
pain
   primary sensory neurons specialized for pain
configurations and forces in musculoskeletal system
   proprioceptive primary sensory neurons
Autonomic Neurons cholinergic
adrenergic
peptidergic
Supporting Cells of Sense Organs and of Peripheral Neurons supporting cells of organ of Corti
   inner pillar cell
   outer pillar cell
   inner phalangeal cell
   outer phalangeal cell
   border cell
   Hensen cell
supporting cell of vestibular apparatus
supporting cell of taste bud
supporting cell of olfactory epithelium
Schwann cell
satellite cell
enteric glial cell
Neurons and Glial Cells of Central Nervous System neurons
glial cells
   astrocyte
   oligodendrocyte
Lens Cells anterior lens epithelial cell
lens fiber
Pigment Cells melanocyte
retinal pigmented epithelial cell
iris pigment epithelial cell
Germ Cells oogonium/oocyte
spermatocyte
Spermatogonium
blast cells
fertilized ovum
Nurse Cells ovarian follicle cell
Sertoli cell
thymus epithelial cell (e.g., reticular cell)
placental cell Administration of Compositions.

Ex vivo delivery of cells transduced with rAAV vectors or infected with rAAV virus is provided for within the invention. Stem cell-mediated ex vivo gene therapy may be used to transplant stimulus-responsive vector system-transduced host stem cells back into the host heart. A suitable ex vivo protocol may include several steps. Adult stem cells may be harvested from the host and any suitable delivery vector may be used to transduce a stimulus-responsive rAAV vector system into the host's own stem cells. These genetically modified cells may then be transplanted back into the host. Several approaches may be used for the reintroduction of stem cells into the host, including jugular vein, tongue vein, intra-pericardial injection and intracardiac intravenous delivery (multiple epicardial puncture or endoventricular injection). Microencapsulation of cells transduced or infected with a stimulus-responsive rAAV vector system modified ex vivo is another technique that may be used within the invention. Autologous and allogeneic cell transplantation may be used according to the invention.

Any suitable delivery method may be used for transducing host stem cells or cardiac cells with a stimulus-responsive rAAV vector system ex vivo. Several suitable modes of delivery are described above and include the following: microinjection, electroporation, calcium phosphate transfection, DEAE dextran transfection, polylysine conjugates, receptor-mediated uptake systems, liposomes, lipid-mediated delivery systems, matrix-impregnated delivery, microparticle encapsulation, intra-cellular targeting ligands, virion-like particles, and viruses.

Effective Doses.

The vectors described above are preferably administered to a mammal in an effective amount, that is, an amount capable of producing a desirable result in a treated subject (e.g., regeneration of myocardium in an infarcted heart). Such a therapeutically effective amount can be determined empirically using experimental animals to determine a dose that results in a desired level of stem cell recruitment to a target tissue. It is expected that an appropriate dosage for intravenous administration of plasmids would be in the range of about 1 µg to 1 mg per site. Different effective dose ranges will vary depending on the weight and bio-responses from the mammals used. These ranges are evident to one of ordinary skill in the art and are within the embodiments of the invention.

Stem Cells.

In conjunction with administration of the above described vector system to a target tissue, to enhance the number of stem cells that home to a target tissue in an animal subject, stem cells can be administered to an animal subject and/or an agent that increases the number of available endogenous stem cells can be administered to the subject. Methods for producing stem cells for transplant are known. Any stem cells suitable for a particular application of the invention may be used. For instance, as described in the Examples section below, stem cells can be isolated from bone marrow according to expression of certain markers. In vitro culture methods can be used to expand the number of these cells. Stem cells isolated, and optionally expanded, in this manner can be administered to an animal (e.g., by intravenous injection, direct delivery to the target tissue, or other suitable means) to increase the number of stem cells available to traffic to the target tissue. To avoid immune system-mediated rejection, the administered stem cells are preferably histocompatible with the host animal. The number of stems cell administered to a given animal subject will depend on the individual situation (e.g., extent of tissue damage, type of tissue, size of animal, health of animal, etc.), but a therapeutic range is expected to be about $1 \times 10^6$ to about $1 \times 10^{10}$ cells.

Because stem cells occur naturally in animals, a step of exogenously administering stem cells to an animal subject is not strictly required (i.e., naturally occurring stem cells will traffic to the treated target tissue without need of an additional step). In many cases, however, the number of available naturally-occurring stem cells may be less than optimal to expedite regeneration of a target tissue. In these cases, the number of stem cells available in the peripheral blood can be increased by known methods. For example, the rate of stem cell movement from the bone marrow to the peripheral blood (i.e., "stem cell mobilization") can be increased by administering to a subject an agent that causes a stem cell to mobilize from the bone marrow. A number of such agents are known. See, e.g., those described in International Application WO 00/50048; and colony stimulating factors such as G-CSF.

Stem Cell Differentiation.

Studies from several species demonstrate that bone marrow-derived stem cells are stem cells for various mesenchymal tissues. The cells are therefore not simply stromal precursors, but precursors of peripheral tissues, such as heart muscle (Pittenger M F, Marshak D R. *Stem Cell Biology*, 949-973, 2001). Normal growth and ultimate stem cell fate depend on engraftment in an appropriate "niche". The mechanism by which the local milieu influences stem cell differentiation is not yet determined. Enhancement of functional activity of a specific organ's niche for heart muscle, e.g., by positive inotropic (pharmacologic augment of contractility) or by positive chronotropic stimuli (heart rate increase by excise), may promote and intensify the transdifferentiation of bone marrow-derived stem cells to a cardiomyocyte phenotype. After an injury (e.g., myocardial infarction), specific factors, including cytokines, stem cell factor, and various growth factors that stimulate cell replication and substitution in the injured tissue are released by surrounding cells. In addition, transplanted stem cells differentiate to cardiomyocytes and begin to express the contractile proteins specific for striated heart muscle, including Desmin, α-myosin, heavy chain, α-Actinin, and phospholamban at levels that are the same as in the host cardiomyocytes. (Strauer B E, Kornowski R *Circulation* 107:929-934, 2003).

Treatment of Various Disease States.

The vector system of the invention can be adapted to a particular disease state by using an appropriate tissue-specific promoter, an appropriate stimulus-responsive element, and appropriate stem cell attracting chemokine genes for regenerating damaged tissue associated with a particular disease state. In the examples described below, this system is employed to direct homing of stem cells to ischemic cardiac tissue. The invention, however, can be directed to treat diseases other than ischemia and to target stem cells to tissues other than the heart. For example, stem cells for replacing damaged pancreatic beta cells in a type 1 diabetic patient can be induced to home to the pancreas using, in conjunction with the above-described SDF-1α-encoding reporter vector, a transactivator vector containing a pancreas-specific promoter and a glucose sensitive element, for example, in addition to the GAL4 DBD and p65 AD sequences. Using this particular system, the transactivator vector detects elevated glucose levels in response to degenerating beta cells; it expresses a chimeric transactivator protein specifically in the pancreas. The transactivator protein then binds to the reporter vector and activates amplified expression of the gene encoding the stem cell-attracting chemokine causing stem cells to traffic to the pancreas. When glucose levels are decreased (i.e., when beta cells have been replaced) the system switches off.

Thus it is clear from the invention described herein that the system is a regulated system which can be switched on or off as needed depending on the stimulus (i.e., decrease/increase in glucose or decrease/increase in oxygen). The present invention overcomes the limitation of the present state of the art by being a homeostasis sensitive system and not a constitutively "turned-on" system described in the state of the art. Moreover, the stem cells recruited into the ischemic heart or damaged liver are anti-apoptotic which is important for tissue repair to replace damaged cells, i.e., are newly generated myocardiocytes or hepatocytes. These cells are natural to the host and do not become rejected or tumorigenic.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

The term "polypeptide" refers to any polymer comprising any number of amino acids, and is interchangeable with "protein", "gene product", and "peptide".

A nucleic acid molecule can be isolated from a natural source, or it can be produced using recombinant DNA technology (e.g., polymerase chain reaction (PCR) amplification, cloning) or chemical synthesis. Nucleic acid molecules can be generated or modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules, and combinations thereof.

Although the phrase "nucleic acid molecule" (or "nucleotide molecule") primarily refers to the physical nucleic acid molecule and the phrase "nucleic acid sequence" primarily refers to the sequence of nucleotides on the nucleic acid molecule, the two phrases can be used interchangeably. As used herein, a "coding" nucleic acid sequence refers to a nucleic acid sequence that encodes at least a portion of a polypeptide (e.g., a portion of an open reading frame), and can more particularly refer to a nucleic acid sequence encoding a polypeptide which, when operatively linked to a transcription control sequence (e.g., a promoter sequence), can express the polypeptide.

The term "operably-linked" or "operatively linked" is used herein to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence.

As used herein, the term "isolated" means removal from its native environment, and can include removal from its immediate native environment.

As used herein, the term "differentiated" refers to those cells that maintain in culture all, or a substantial amount of, their specialized structure and function typical of the cell type in vivo. Partially differentiated cells maintain less than a substantial amount of their full complement of specialized structure and/or function.

Nucleic acid constructs comprising a gene switch/biosensor and a nucleic acid sequence encoding a stem cell-attracting chemokine, which is expressed in response to a stimulus that is present in injured but not health tissue, may be introduced into stem cells, progenitor cells, or mature (differentiated) cells, for example. As used herein, the term "stem cell" is an unspecialized cell that is capable of replicating or self renewal, and developing into specialized cells of a variety of cell types. The product of a stem cell undergoing division is at least one additional stem cell that has the same capabilities of the originating cell. For example, under appropriate conditions, a hematopoietic stem cell can produce a second generation stem cell and a neuron. Stem cells include embryonic stem cells (e.g., those stem cells originating from the inner cells mass of the blastocyst) and adult stem cells (which can be found throughout the more mature animal, including humans). As used herein, stem cells are intended to include those stem cells found in animals that have matured beyond the embryonic stage (e.g., fetus, infant, adolescent, juvenile, adult, etc.). The list of tissues reported to contain stem cells is growing and includes, for example, bone marrow, peripheral blood, brain, spinal cord, umbilical cord blood, amniotic fluid, placenta, dental pulp, blood vessels, skeletal muscle, epithelia of the skin and digestive system, cornea, retina, liver, and pancreas.

As used herein, the term "progenitor cell" (also known as a precursor cell) is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the term "phenotype" refers to all the observable characteristics of a cell (or organism); its shape (morphology); interactions with other cells and the non-cellular environment (e.g., extracellular matrix); proteins that appear on the cell surface (surface markers); and the cell's behavior (e.g., secretion, contraction, synaptic transmission).

As used herein, the terms "administer", "apply", "treat", "transplant", "implant", "deliver", and grammatical variations thereof, are used interchangeably to provide vectors of the subject invention to target cells in vitro (e.g., ex vivo) or in vivo, or provide genetically modified cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents.

Unless otherwise defined, all technical terms used herein have the same meaning as commonly understood by one or ordinary skill in the art to which this invention belongs. Commonly understood definitions of molecular biology terms can be found in Rieger et al., Glossary of Genetics: Classical and Molecular, $5^{th}$ edition, Springer-Verlag: New York, 1991; and Lewin, Genes V, Oxford University Press: New York, 1994. Commonly understood definitions of virology terms can be found in Granoff and Webster, Encyclopedia of Virology, $2^{nd}$ edition, Academic Press: San Diego, Calif., 1999; and Tidona and Darai, The Springer Index of Viruses, $1^{st}$ edition, Springer-Verlag: New York, 2002. Commonly understood definitions of microbiology can be found in Singleton and Sainsbury, Dictionary of Microbiology and Molecular Biology, 3$^{rd}$ edition, John Wiley & Sons: New York, 2002.

Although methods and materials similar or equivalent to those described herein can be used in the practice or testing of the present invention, suitable methods and materials are described below.

EXAMPLES

The invention can be illustrated by the following examples in which a dual plasmid vector system is used to detect and respond to hypoxia in cardiac tissue. The first plasmid is the "transactivator" plasmid. This contains a cardiac-specific promoter linked to a sequence encoding an oxygen-sensitive chimeric transactivator that includes a GAL4 DBD, an ODD, and a p65 AD. The second plasmid is the "reporter" plasmid which contains a gene encoding hSDF-1α (a stem cell attracting chemokine) linked to a GAL4 UAS. The "transactivator" plasmid expresses the chimeric transactivator specifically in the heart. In response to hypoxia, the transactivator binds to the GAL4 UAS sequence in the reporter plasmid, resulting in the expression of the hSDF-1α gene. The resulting high local concentration of hSDF-1α gene results in higher levels of homing of stem cells to the damaged tissue.

Example 1

Construction of Plasmids

To make the transactivator plasmid, the ODD (amino acids 394-603; see Huang et al. *Proc Natl Acad Sci USA*. 95:7987, 1998) was amplified by PCR from pCEP4/HIF-1alpha (Semenza et al. *J Biol Chem.* 271:32529, 1996) and inserted in frame between the coding sequence of GAL4 DBD and p65AD in pGS-MLC to generate pGS-MLC-ODD (see FIG. 1). pGS-CMV is a plasmid that expresses a chimeric transcription factor consisting of the yeast GAL4 DBD (amino acids 1-93; Keegan et al., *Science*. 231:699, 1986) and the human p65AD (amino acids 283-551; Schmitz et al., *EMBO J.* 10:3805, 1991) from NF-κB under the control of a 281 bp MLC-2v promoter.

The reporter plasmid, pGene-hSDF-1α-6his (FIG. 1), encodes stem cell-attracting chemokine SDF-1α driven by six copies of a 17 bp GAL4 UAS (Giniger et al., *Cell*. 40:767, 1985) and an adenovirus E1b TATA box (Lillie and Green, *Nature*. 338:39, 1989). It was derived from pGene/V5-His/lacZ (INVITROGEN, Carlsbad, Calif.) by replacing the lacZ coding sequence with a hSDF-1α cDNA. The identity of clones was confirmed by nucleotide sequence analysis.

Example 2

Testing the Plasmids In Vivo

Figure 2:
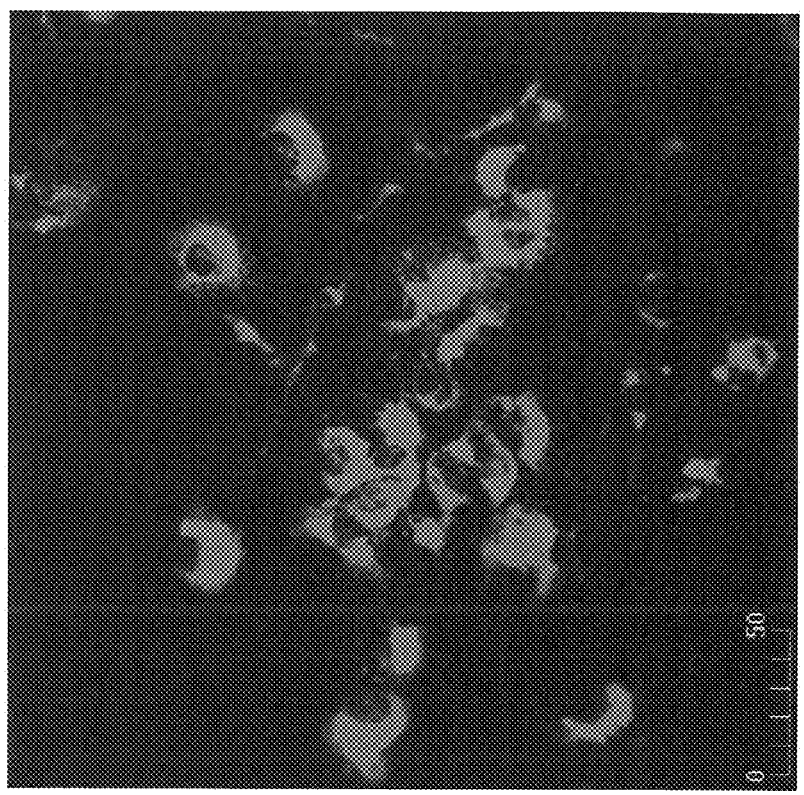
FIG. 2 is a photomicrograph showing the morphologic features of mice bone marrow Lin$^-$c-kit$^+$ cells after labeling with PKH26. The labeling efficiency of Lin$^-$c-kit$^+$ cell was approximately 100%.

Preparation of bone marrow stem cell—Bone marrow was harvested from femur and tibia of BALB/c mice. Mononuclear cells isolated from bone marrow were sorted to separate Lin⁻ cells with Lin cocktail by SPINSEP cell enrichment procedure (Stem Cell Technologies Inc., Vancouver, Canada). The Lin⁻ bone marrow stem cells were enriched for c-kit⁺ cells using a c-kit MACS microbead system (MACS bead and apparatus from Dynal Biotech, Oslo, Norway; biotin-conjugated rat anti-mouse c-kit monoclonal antibody from BD biosciences, San Jose, Calif.). After isolation the Lin⁻c-kit⁺ cells were resuspended in staining medium containing PKH26-GL (Sigma Company, St. Louis, Mo.). Referring to FIG. 2, the mouse Lin⁻c-kit⁺ stem cells were relatively homogenous in appearance. The labeling efficiency with PKH26 was approximately 100%.

MI generation, gene therapy, and stem cell therapy—Age-matched 8-week-old BALB/c mice were used in a MI model. Mice were anesthetized, intubated and mechanically ventilated. A thoracotomy incision was made in the fourth intercostals space and the proximal left anterior descending (LAD) coronary artery was surgically occluded with an 8-0 non-absorbable suture. Successful coronary occlusion was confirmed by a change of ST segment on the EKG from a limb lead. In sham mice, ligation was placed beside the coronary artery. Simultaneously, adult BALB/c mice (n=10/group) were injected intra-myocardially with two plasmids: pGS-MLC-ODD (40 µg) and pGene-SDF-1α-6his (20 µg), while control mice (n=10) received saline injection only. PKH26-labeled Lin⁻c-kit⁺ stem cells were systemically injected into the mice.

Western blot—Heart and other tissue samples from the mice were homogenized in Tris (12.5 mM/l) buffer (pH 6.8) containing glycerol (10%), SDS (4%), and β-mercaptoethanol (1.8%). Twenty-five µg of soluble protein from each sample was separated by gel electrophoresis (using a 12% Ready Gel gel from BIORAD, Calif., USA), and Western blotting was carried out using and antibody to His (C-term) (1:1,000, INVITROGEN Inc., Carlsbad, Calif.). The relative amounts of hSDF-1α protein expression were determined by densitometric analysis.

Assessment of SDF-1α and identification of stem cells in the heart—Hearts were collected from the experimental animals 1 week after MI for detection of SDF-1α expression and identification of stem cells that localized to ischemic heart tissue. The expression of SDF-1α in ischemic heart tissue was detected by immunohistochemistry using an antibody to hSDF-1α or 6his using DAKO EnVision Systems Alkaline Phosphatase kit (DAKO, Cambridge, Mass.). Confocal imaging and immunofluorescent staining was also used to identify both the expression of hSDF-1α (using a FITC-labeled secondary antibody) and the labeled transplanted stem cells (previously labeled with PKH26).

Example 3

Results

Figure 3:
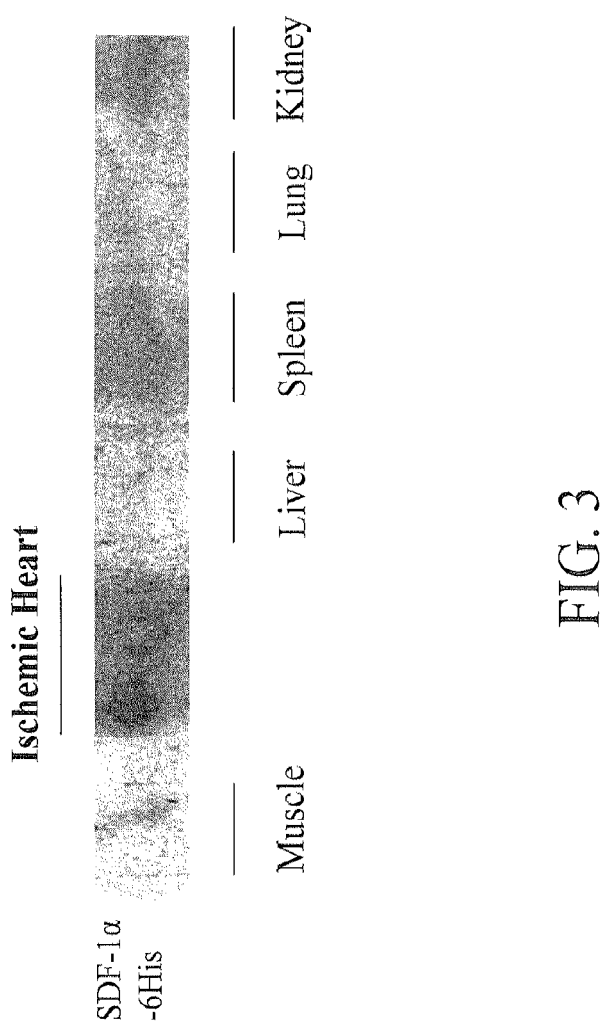
FIG. 3 is a Western blot analysis showing an increased amount of tissue-specific hSDF-1α expression in the ischemic mouse heart tissue compared to hSDF-1α in the spleen, liver, lung, kidney, and muscle at 1 week after plasmid injection.
Figure 4A:
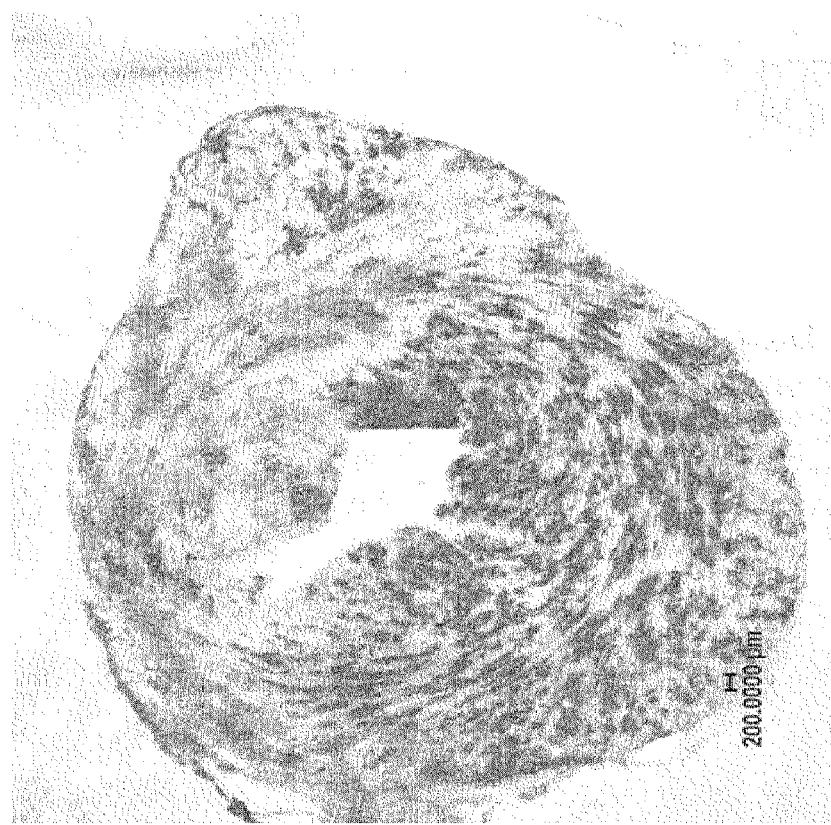
FIGS. 4A and 4B are photomicrographs showing immunohistochemical localization of hSDF-1 protein in cross-section of papillary muscle level 7 days after vigilant hSD F-1 plasmid transfer. Expression of hSDF-1 could be seen in the peri-infarct zone of ischemic myocardium in vigilant hSDF-1 plasmid treated MI group (FIG. 4A) with less-hSDF-1 expression in vigilant treated non-MI group (FIG. 4B).
Figure 4B:
Figure 5A:
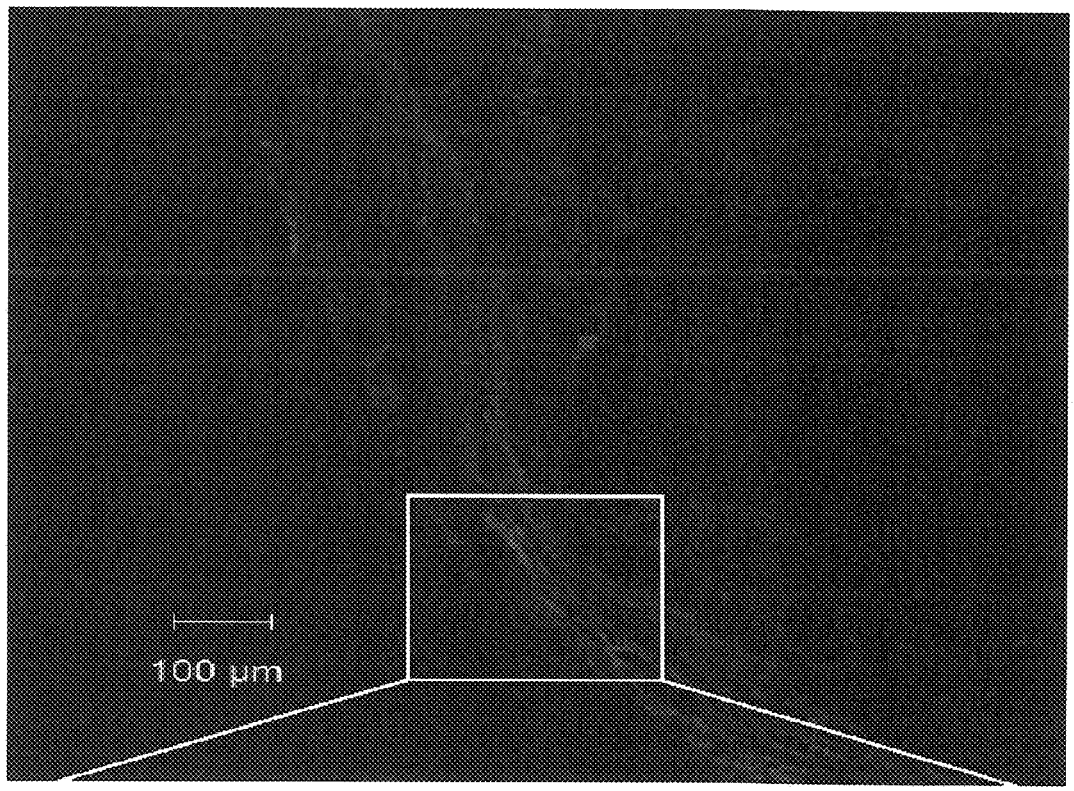
FIGS. 5A-5D are photomicrographs of ischemic myocardium.
Figure 5B:
Figure 5C:
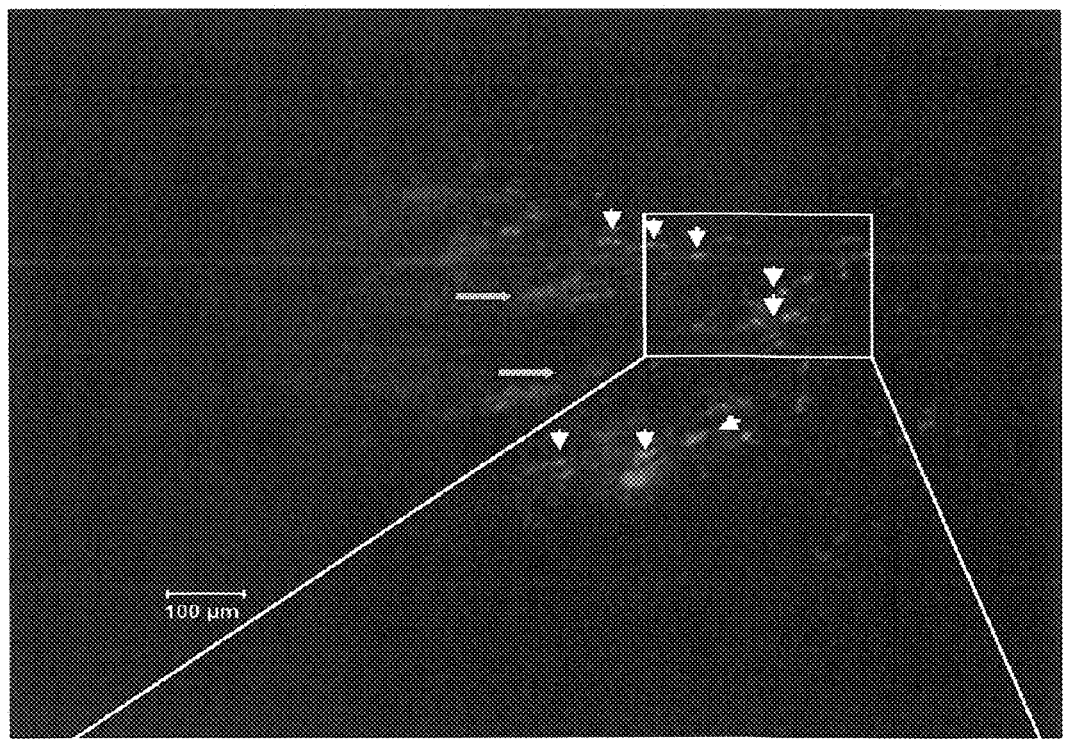
Figure 5D:
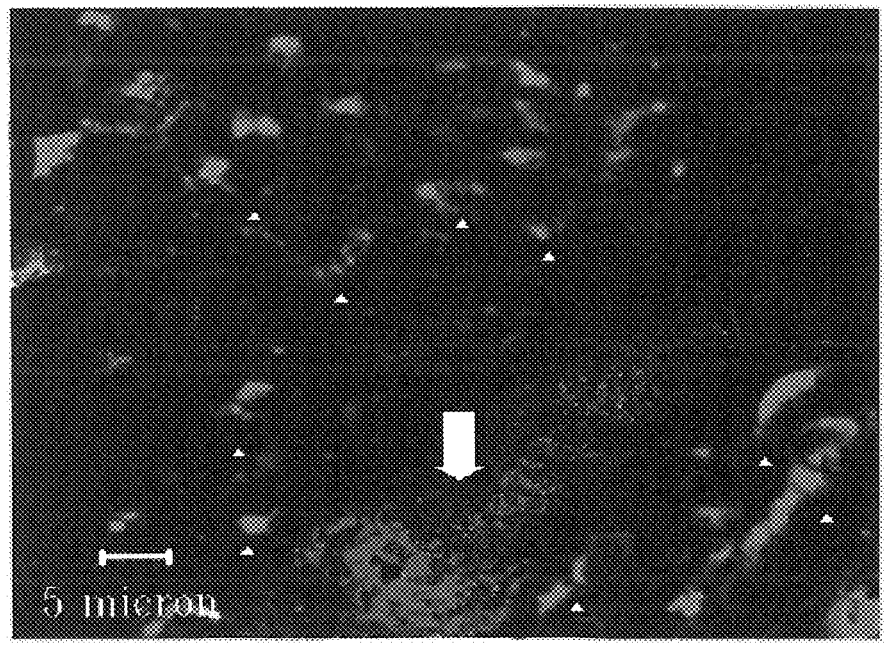
Figure 6:
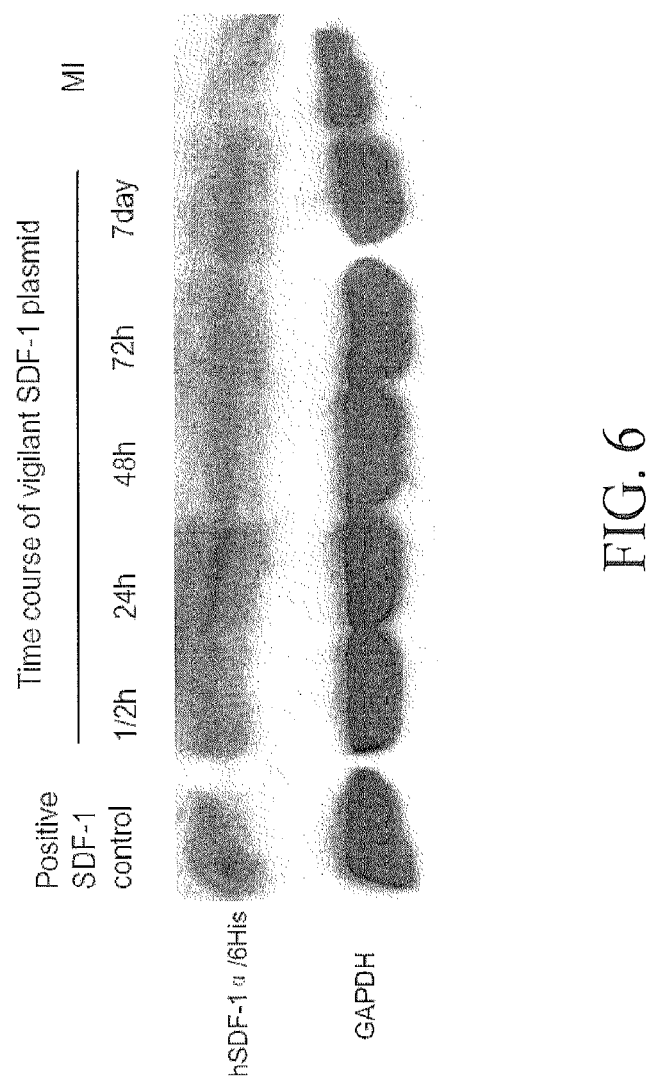
FIG. 6 shows the effect of myocardial ischemia on hypoxia-induced hSDF-1 protein expression in mouse heart. The mouse heart underwent ischemia for one-half hour, 24 hours, 48 hours, 72 hours and 7 days. After left ventricular ischemia, the heart was analyzed for hSDF-1/6× His protein expression. GAPDH confirmed the integrity and equal loading of protein. The time course of vigilant SDF-1 vector expression shows the hSDF-1 protein reached a peak in 24 hours after gene treatment. At 7 days, the expression of vigilant SDF-1 was stronger than endogenous SDF-1 expression. Positive SDF control is SDF-1 plasmid that can constitutively express SDF-1.
Figure 7A:
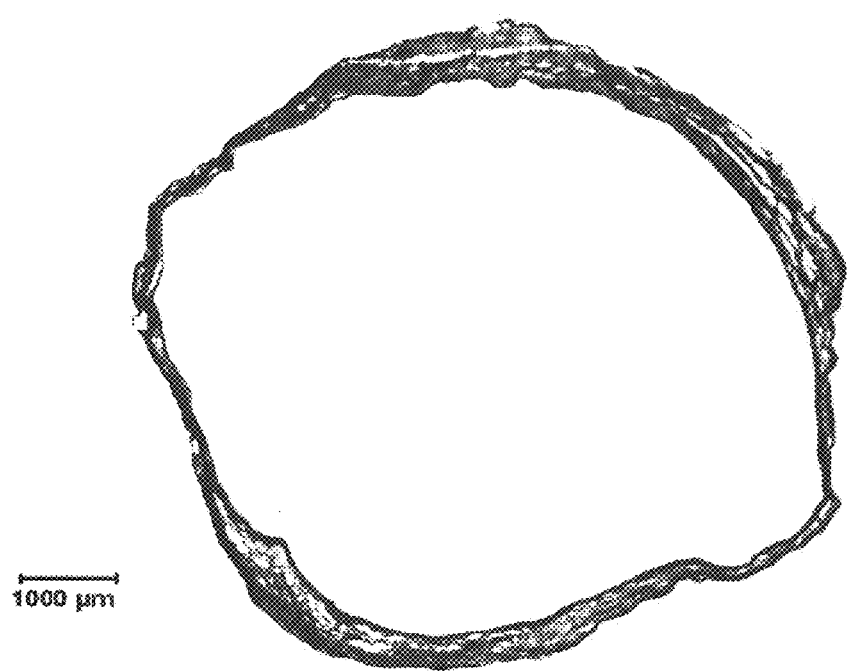
FIGS. 7A-7D are photomicrographs showing that expression of hSDF-1 in ischemic myocardium mobilizes labeled Lin-c-Kit+ HSC cells (red) surrounding the cardiomyocytes's expression of hSDF-1 (green). It was observed that groups of cells were positively stained for hSDF-1, and attracted more HSC, around the site in the vigilant hSDF-1-treated MI group (FIGS. 7B and 7D), while less SDF-1 expression and few mobilized HSC could been seen in the medium-treated MI group (FIGS. 7A and 7C).
Figure 7B:
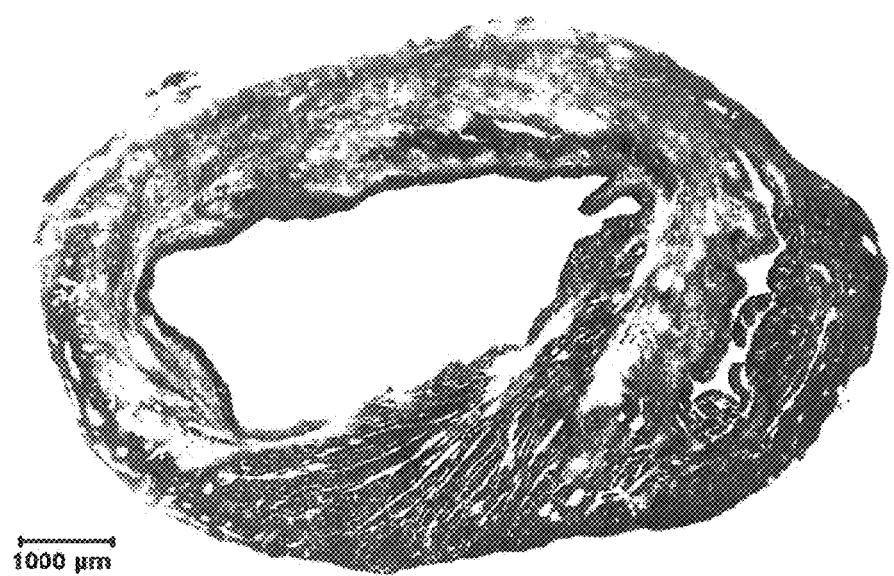
Figure 7C:
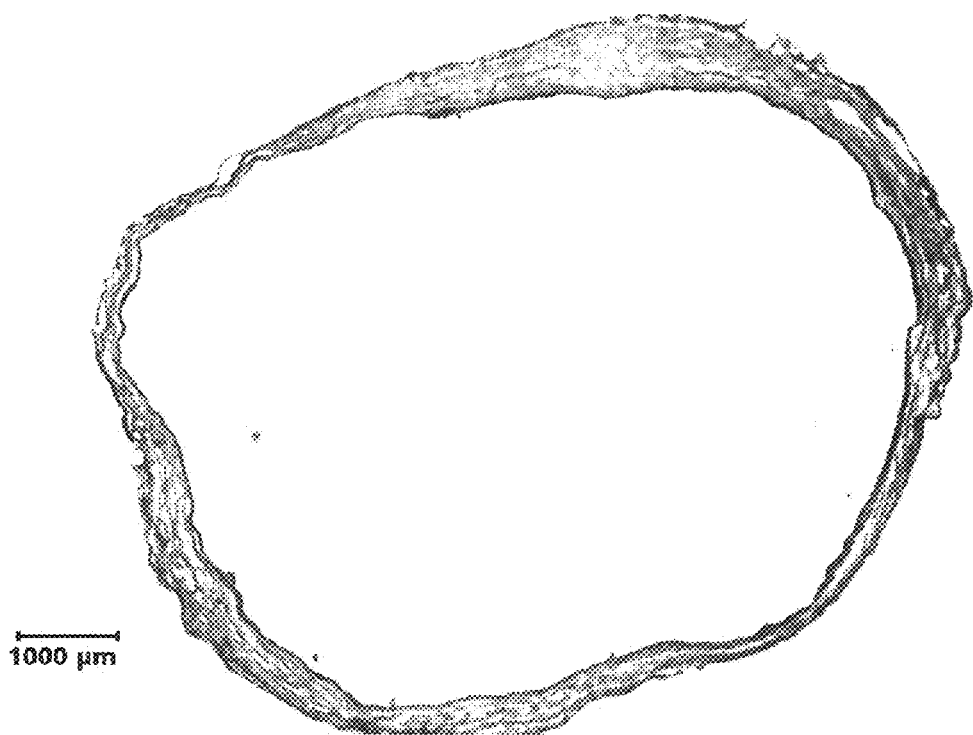
Figure 7D:
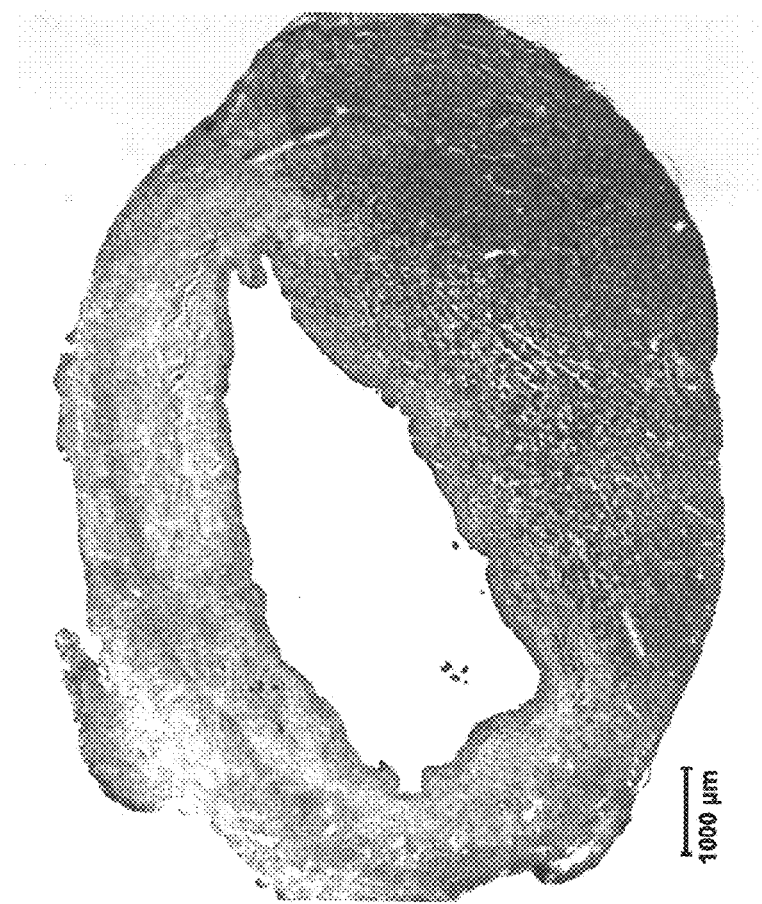
Figure 8A:
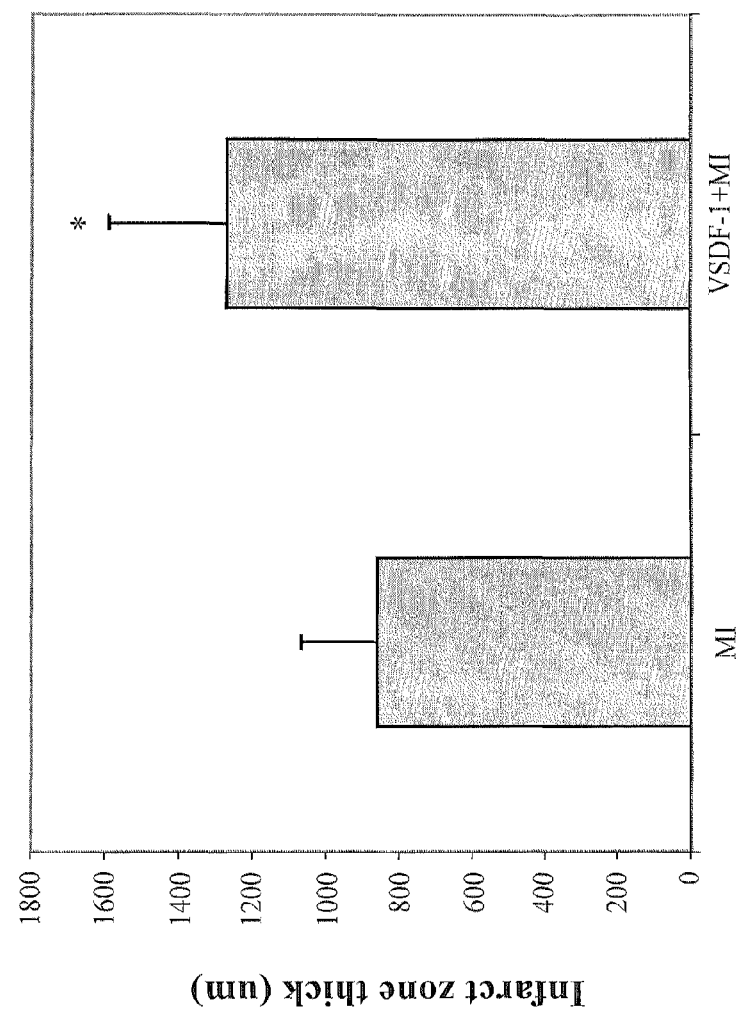
FIGS. 8A and 8B are bar graphs showing the infarct zone thickness (FIG. 8A) and infarct size (percentage) (FIG. 8B) in the ischemic myocardium shown in FIGS. 7A-7D, treated with vigilant hSDF-1 (VSDF-1+MI) and medium (MI; control).
Figure 8B:
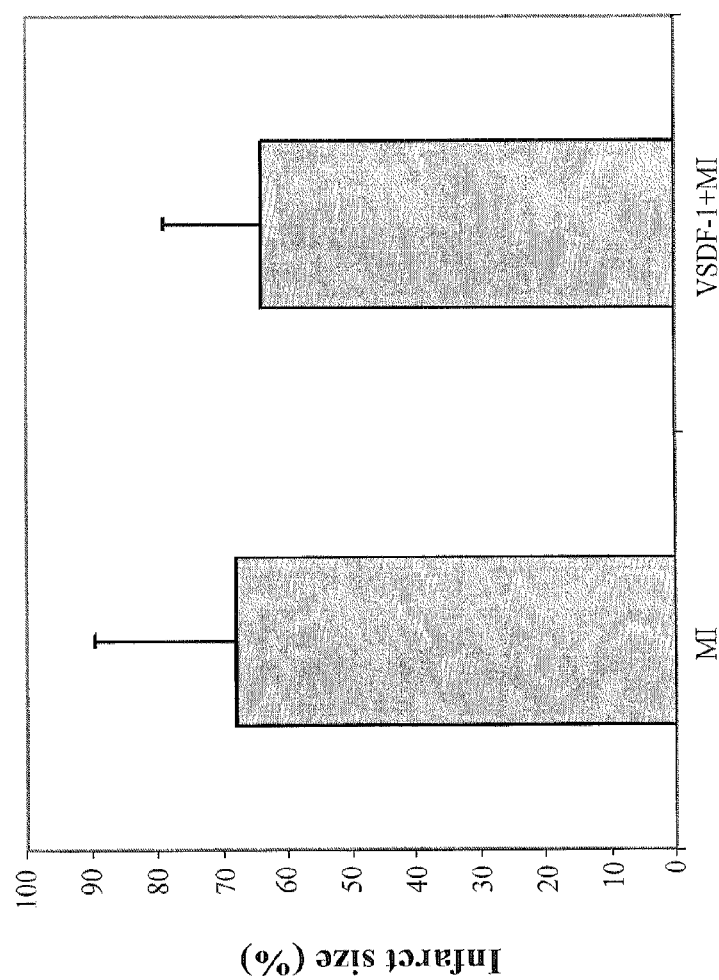
Figure 9A:
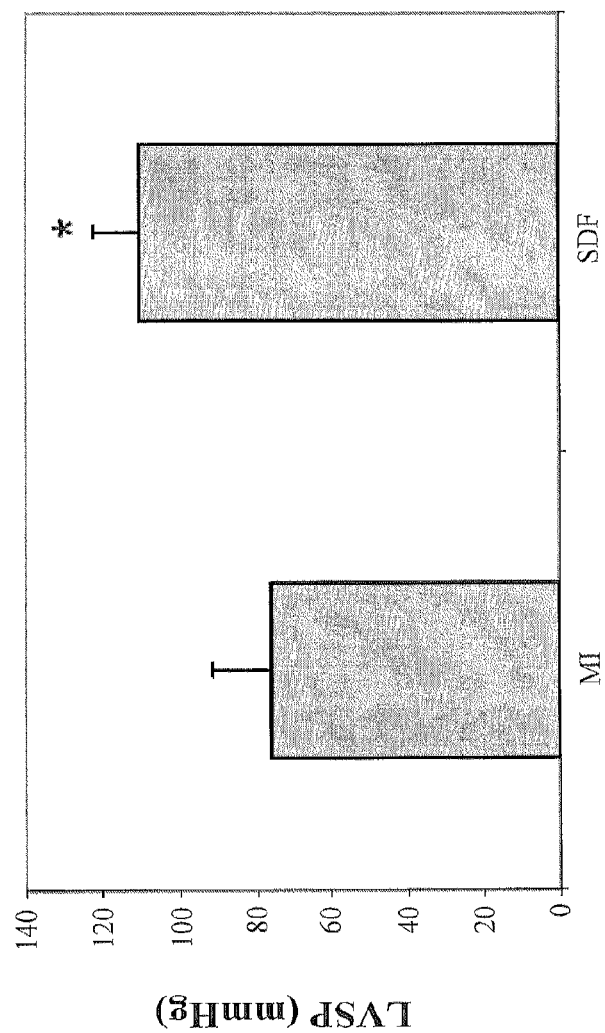
FIGS. 9A-9D are bar graphs showing that MSCs implantation improves left ventricular function. Both LV systolic performance (LVSP) and diastolic performance (LVDP), as assessed by maximum and minimum dP/dt, respectively, were greatest in the vigilant hSDF-1 group (maximum dP/dt 3004.6±362.7 in medium control vs 4057.8±821.4 in vigilant hSDF-1, p=0.0015 (FIG. 9C); minimum dP/dt– 2447.2±621.9 in medium control vs –3223.0±455.9 in vigilant hSDF-1, p=0.037) (FIG. 9D), indicating that both systolic and diastolic functions were best preserved in the vigilant hSDF-1$_{group}$ after myocardial infarction versus medium group.
Figure 9B:
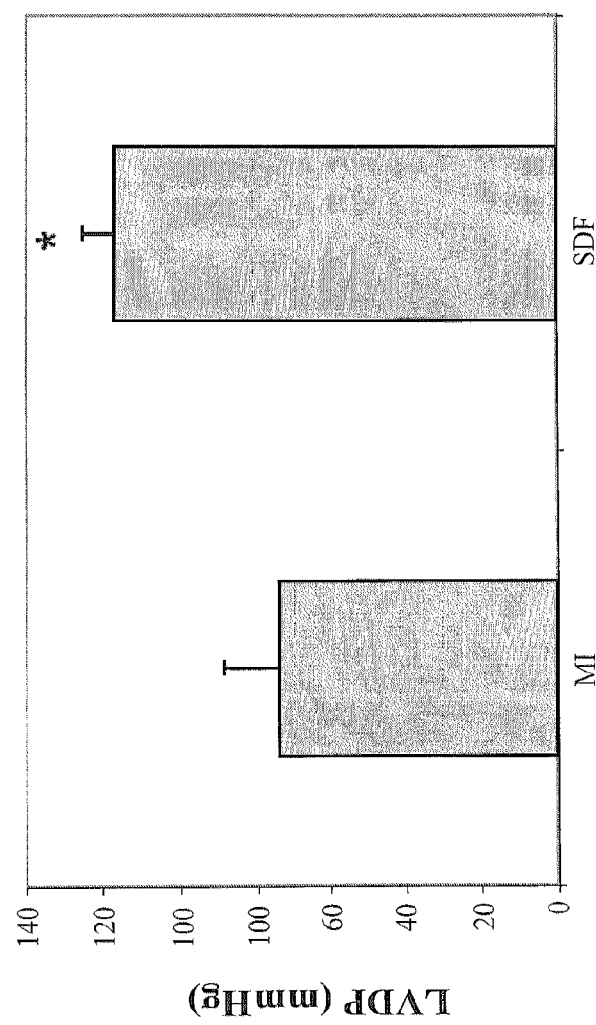
Figure 9C:
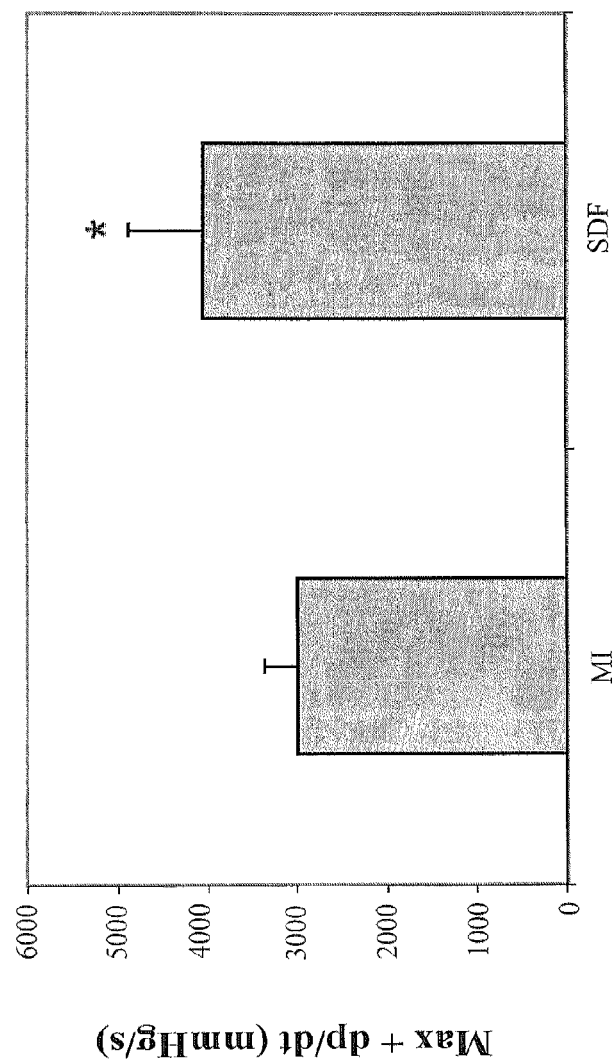
Figure 9D:
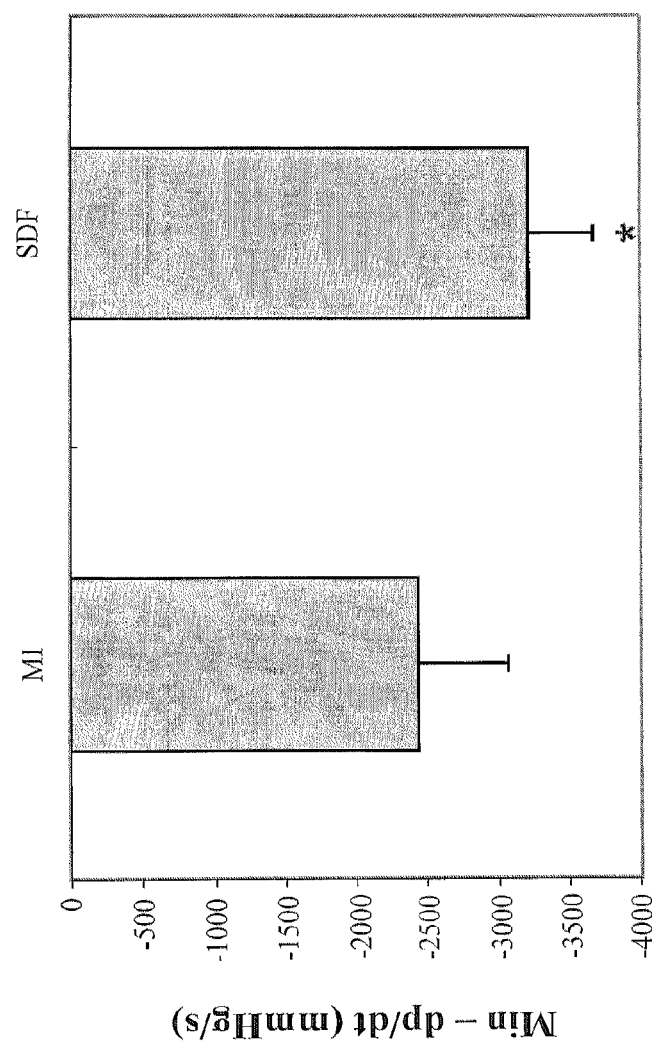

Mice whose hearts were transfected with the MLC-ODD dual plasmid system then subjected to ischemia by ligation of LAD showed higher tissue-specific expression of hSDF-1α in the ischemic mouse heart tissue than in the spleen, liver, lung, kidney and muscle at 1 week after intracardiac plasmid injection (see Western blot shown in FIG. 3). One week after intracardiac injection of plasmid, immunohistochemical staining showed that hSDF-1α was clearly present in ischemic myocardium (FIG. 4A) of mice and absent in the control (mice that did not undergo MI; FIG. 4B). Transplanted stem cells were attracted to the SDF-1α-expressing peri-infarct zone (the ischemic tissue) in a dose-dependent manner with increasing time (FIGS. 5A-5D). This amplification did not compromise the cardiac specificity of MLC-2v promoter, which still maintained the previously observed expression profile (i.e., higher in ischemic heart than in the non-cardiac tissues).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A composition comprising:
   (a) a first polynucleotide comprising:
      (1) a gene switch/biosensor comprising a nucleic acid sequence encoding a physiological stimulus-sensitive chimeric transactivator, wherein said physiological stimulus-sensitive chimeric transactivator is oxygen-sensitive and comprises a GAL4 DNA-binding, domain (DBD), an oxygen-dependent degradation domain (ODD), and a p65 activation domain (p65 AD), and
      (2) an operatively linked tissue-specific promoter; and
   (b) a second polynucleotide comprising a nucleic acid sequence encoding a stem cell-attracting chemokine, wherein said second polynucleotide further comprises a GAL4 upstream activating sequence (UAS) linked to said nucleic acid sequence of said second polynucleotide, and wherein in response to hypoxia, said transactivator binds to the GAL4 UAS, resulting in expression of said nucleic acid sequence encoding said stem cell-attracting chemokine.

2. The composition of claim 1, wherein said tissue-specific promoter is specific for expression in a tissue selected from the group consisting of kidney, epithelial tissue, endothelial tissue, liver, brain, neural tissue, thymus, and pancreas.

3. The composition of claim 1, wherein said tissue-specific promoter is selected from the group consisting of CLCN5, rennin, androgen-regulated protein, sodium-phosphate cotransporter, renal cytochrome P-450, parathyroid hormone receptor, kidney-specific cadherin, E-cadherein, estrogen receptor (ER) 3, endoglin, ICAM-2, human phenylalanine hydroxylase (PAH), human C-reactive protein (CRP), human enolase (ENO3), thy-1 antigen, gamma-enolase, glial-specific glial fibrillary acidic protein (GFAP), human FGF1, GATA transcription factor, and pancreas duodenum homeobox 1 (PDX-1).

4. The composition of claim 1, wherein said tissue-specific promoter is a cardiac-specific promoter.

5. The composition of claim 1, wherein said tissue-specific promoter is a cardiac-specific promoter selected from the group consisting of the ventricular form of the MLC-2v promoter, a fragment of the native MLC-2v promoter, alpha myosin heavy chain promoter, and myosin light chain-2 promoter.

6. The composition of claim 1, wherein said stem cell-attracting chemokine is selected from the group consisting of SCF, vascular endothelial growth factor (VEGF), granulocyte colony-stimulating factor (G-CSF), an integrin, and hSDF-1alpha.

7. The composition of claim 1, wherein said stem cell-attracting chemokine comprises hSDF-1alpha.

8. The composition of claim 1, wherein said physiological stimulus is associated with cell injury.

9. The composition of claim 1, wherein said composition is a recombinant viral vector.

10. The composition of claim 1, wherein said composition is a recombinant viral vector selected from an adenovirus, an adeno-associated virus, a herpes simplex virus, a lentivirus, or a retrovirus.

11. The composition of claim 1, wherein said composition is a recombinant adeno-associated viral vector.

12. The composition of claim 1, wherein said composition is a non-viral vector.

13. The composition of claim 1, wherein said composition is a plasmid.

14. The composition of claim 1, wherein said second polynucleotide further comprises a TATA element.

15. The composition of claim 1, wherein said second polynucleotide comprises at least two copies of said GAL4 upstream activating sequence (UAS).

* * * * *

UNITED STATES PATENT AND TRADEMARK OFFICE
CERTIFICATE OF CORRECTION

PATENT NO. : 8,569,471 B2
APPLICATION NO. : 13/299991
DATED : October 29, 2013
INVENTOR(S) : Phillips et al.

Page 1 of 1

It is certified that error appears in the above-identified patent and that said Letters Patent is hereby corrected as shown below:

In the Specification

Column 6,
Line 2, Delete "(see, Feigner" and insert --(see, Felgner--

Signed and Sealed this
Fifteenth Day of April, 2014

Michelle K. Lee
*Deputy Director of the United States Patent and Trademark Office*